United States Patent
Dibiasi et al.

(10) Patent No.: US 6,200,296 B1
(45) Date of Patent: Mar. 13, 2001

(54) 5MM INJECTION NEEDLE

(75) Inventors: Michael A. Dibiasi, West Milford; Robert E. West, Morristown, both of NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 08/869,612

(22) Filed: Jun. 5, 1997

Related U.S. Application Data

(63) Continuation-in-part of application No. 08/721,368, filed on Sep. 26, 1996.

(51) Int. Cl.⁷ .................................................. A61M 5/32
(52) U.S. Cl. ................................................ 604/272; 604/117
(58) Field of Search .................................. 604/272, 187, 604/117, 232, 192, 263

(56) References Cited

U.S. PATENT DOCUMENTS

| | | | |
|---|---|---|---|
| 4,313,439 | 2/1982 | Babb et al. | 128/214 |
| 4,552,561 | 11/1985 | Eckenhoff et al. | 604/896 |
| 4,692,142 | * 9/1987 | Dignam et al. | 604/117 X |
| 4,894,054 | 1/1990 | Miskinyar | 604/136 |
| 4,917,670 | 4/1990 | Hurley et al. | 604/51 |
| 4,944,677 | 7/1990 | Alexandre | 433/165 |
| 4,969,884 | 11/1990 | Yum | 604/892 |
| 4,973,318 | 11/1990 | Holm et al. | 604/896 |
| 5,015,235 | 5/1991 | Crossman | 604/117 |
| 5,151,093 | 9/1992 | Theeuwes et al. | 604/892 |
| 5,279,586 | 1/1994 | Balkwill | 604/232 X |
| 5,295,976 | 3/1994 | Harris | 604/21 |
| 5,374,256 | 12/1994 | Kriesel | 604/232 |
| 5,462,535 | 10/1995 | Bonnichsen et al. | 604/272 |
| 5,540,357 | * 7/1996 | Kurjan et al. | 604/117 X |
| 5,599,323 | 2/1997 | Bonnichsen et al. | 604/272 |
| 5,709,668 | * 1/1998 | Wacks | 604/232 |
| 5,951,530 | 9/1999 | Steengaard et al. | 604/272 |
| 5,984,906 | 11/1999 | Bonnichsen et al. | 604/272 |

FOREIGN PATENT DOCUMENTS

| | | |
|---|---|---|
| 279583 B1 | 10/1993 | (EP) . |
| 0702970 A2 | 3/1996 | (EP) . |
| 3-275214 | 12/1991 | (JP) . |
| 4-502877 | 5/1992 | (JP) . |
| 6-86745 | 12/1994 | (JP) . |
| WO 90/07348 | 7/1990 | (WO) . |
| 92/17131 | 10/1992 | (WO) . |
| 93/00948 | 1/1993 | (WO) . |
| 93/07877 | 4/1993 | (WO) . |
| WO 93/07922 | 4/1993 | (WO) . |
| WO 95/12425 | 5/1995 | (WO) . |

OTHER PUBLICATIONS

"Announcing The New Micro–Fine IV Pen Needle", pp. BD 386–BD 389, published Jul. 1, 1991.

Australian Standard 2145–1985, "Hypodermic Equipment–Hypodermic Needle Tubing", published by The Standards Association of Australia, Jul. 12, 1985, pp. 24–37.

NovoFine 30G 8mm, "NovoFine reduces pain and the risk of intramuscular injections", pp. 18.1–18.4, May, 1993.

United States Court of Appeals for the Federal Circuit Civil Action 98–1312, –1313, Novo Nordisk A/S, Novo Nordisk of North America, Inc., and *Novo Nordisk Pharmaceuticals, Inc., v. Eli Lilly and Co.*, and Becton Dickinson and Company, Decided Feb. 23, 1999.

(List continued on next page.)

*Primary Examiner*—John D. Yasko
(74) *Attorney, Agent, or Firm*—Fitzpatrick, Cella, Harper & Scinto

(57) ABSTRACT

A needle assembly for a medication delivery pen or hypodermic syringe having a usable length of 5 mm (0.197") that delivers a dose of medication to a proper location in the tissue "strata" or subcontinuous layer without the need for the user or patient to "pinch-up" the skin layer during the injection.

10 Claims, 3 Drawing Sheets

OTHER PUBLICATIONS

Insuject–Insuject–X, The Insulin Pens from Nordisk–Wellcome, Freedom of Choice–Freedom of Lifestyle, pp. BD 17378, –BD 17395, c. 1988–1989.

Novolin Pen, Dial–A–Dose Insulin Delivery System, Teaching Manual, Squibb Novo, pp. BD 15360 –BD 15373, 1988.

Diabetic Medicine, J. C. Thow, et al., "Different Absorption of Isophase (NPH) Insulin from Subcutaneous and Intramuscular Sites Suggests a Need to Reassess Recommended Insulin Injection Technique", 1990 pp. 600–602.

Diabetic Medicine, J. E. Henriksen, et al, "Absorption of NPH (Isophane) Insulin in Resting Diabetic Patients: Evidence for Subcutaneous Injection in the Thigh as the Preferred Site", 1991, pp. 453–457.

Diabetes Care, John P. Bantle, et al., "Effects of the Anatomical Region Used for Insulin Injections on Glycemia in Type I Diabetes Subjects", 1993, vol. 16, pp. 1592–1596.

Diabetologia, J. E. Henriksen, et al., "Impact of Injection Sites for Soluble Insulin on Glycaemic Control in Type 1 (insulin–dependent) Diabetic Patients Treated with a Multiple Insulin Injection Regimen", 1993, pp. 752–758.

Diabetes Care, Jiten P. Vora, et al., "Relationship Between Absorption of Radiolabeled Soluble Insulin, Subcutaneous Blood Flow, and Anthropometry", 1992, vol. 15, pp. 1484–1493.

Archives of Disease in Childhood, C. P. Smith, et al., "Subcutaneous or Intramuscular Insulin Injections", 1991, pp. 879–882.

Diabetic Medicine, P.H.E.M. de Meijer, et al., "The Variability of the Absorption of Subcutaneously Injected Insulin: Effect of Injection Technique and Relation with Brittleness", 1990, pp. 499–505.

Diabetes Care, Michel Polak, et al, "Subcutaneous or Intramuscular Injections of Insulin in Children", 1996, vol. 19, pp. 1434–1436.

Diabetic Medicine, A. Vaag, et al., "Intramuscular Versus Subcutaneous Injection of Unmodified Insulin: Consequences for Blood Glucose Control in Patients with Type 1 Diabetes Mellitus", 1990, pp. 335–342.

Diabetes Care, Allan Vaag, et al, "Variation in Absorption of NPH Insulin", 1990, vol. 13, pp. 74–76.

Scand J. Caring Science, Lars Engstrom, et al., "Short Communication", 1993, pp. 57–59.

Diabetes Care, Anders Frid, et al., "Effects of Accidental Intramuscular Injection on Insulin Absorption in IDDM", 1988, vol. 11, pp. 41–45.

Diabetic Medicine, J. C. Thow, et al., "Insulin Injection Site Tissue Depths and Localization of a Simulated Insulin Bolus Using a Novel Air Contrast Ultrasonographic Technique in Insulin Treated Diabetic Subjects", 1992, pp. 915–920.

Diabetes Care, Per Hildebrandt, et al., "The Absorption of Subcutaneously Injected Short–Acting Soluble Insulin: Influence of Injection Technique and Concentration", 1983, vol. 6, pp. 459–462.

Applied Radiology, Jun. 1994, vol. 23, No. 6., advertisement for Ranfac corporation.

The Journal of Pharmacology and Experimental Therapeutics, Dorothea E. Blandford et al., "Role of Vasopressin in Response to Intrarenal Infusions of *Alpha*–2 Adrenoceptor Agonists", vol. 255, No. 1 (1990).

The Journal of Pharmacology and Experimental Therapeutics, D. D. Smyth et al., Opposite Rank Order of Potency for *Alpha*–2 Adrenoceptor Agonists on Water and Solute Excretion in the Rat: Two Sites and/or Receptors; vol. 261, No. 3 (1992).

BMJ, "Insulin Injection Technique", Jonathan Thow, et al., vol. 301, Jul. 7, 1990.

In the Matter of: Novo Nordisk v. Becton Dickinson and Co.; Trial vol. 9, May 25, 2000, pp. 1231–1234.

Brochure, "The Outstanding Insulin Cartridge for the Insuject System", BD 017384–BD 017395, c. 1988–1989.

Novo Nordisk A/S, Novo Nordisk of North America, Inc. and Novo Nordisk Pharmaceuticals Inc. v. Becton Dickinson and Company, 96 Civ. 9506 (BSJ), Declarations of Arthur D. Dawson, Ph.D, Fred Cassel, and Justin Boylan, and attached Exhibits 47–49.

International Standard, ISO 9626, "Stainless Steel Needle Tubing for Manufacture of Medical Devices", pp. 2630–2639; Sep. 1, 1991.

The Advanced Approach to Insulin Injection, The individually Adapted and Flexible Insulin Therapy, BD 000551–BD 000554, Jun., 1987.

"State–of–the–art, Injection Technology from Switzerland", BD 000555–000558, 1998.

Product Information, Terumo Insulin Syringe, published c.1989, p. Nov 0034714.

Novo Nordisk internal memorandum dated Oct. 23, 1989 re: testing of Terumo 29 gauge syringes having measured inner diameter of 0.13–0.15mm.

OPINION & ORDER, 96 Civ. 9506 (BSJ), Mar. 9, 1998 (USDC, SDNY).

Hypodermic Disposable Needles: Mechanical Properties and Pain Perception as a Function of Needle Diameter: Lene Lytzen Jun. 1991.

Photocopy of package for Terumo needle sold in 1989, having needle internal diameter 0.13 to 0.15 mm.

Adverstising Brochure for Terumo 29 Gauge Insulin Syringe, Diabetes Educator, Jan.–Feb. 1989, p. Nov 0034718.

* cited by examiner

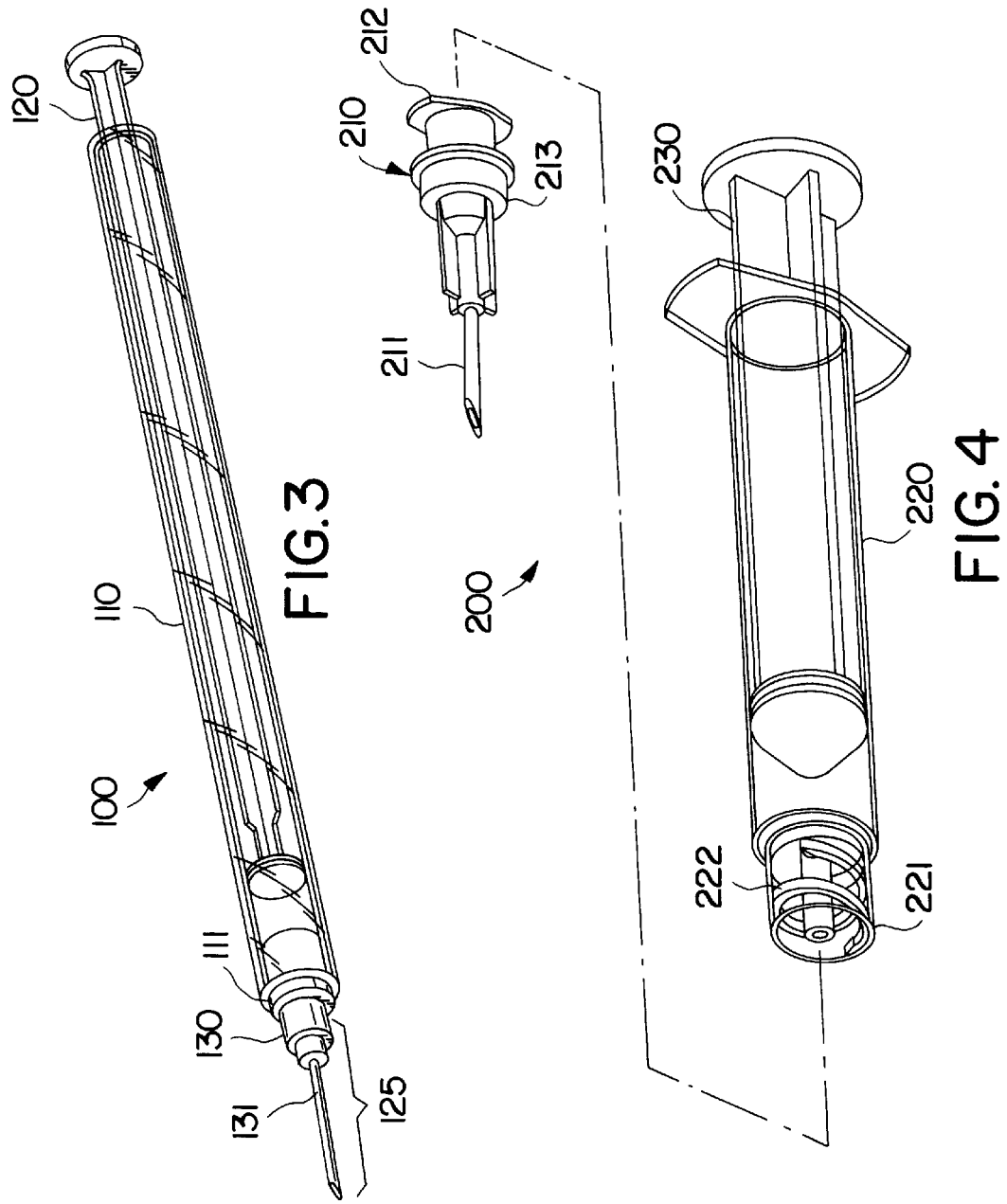

5MM INJECTION NEEDLE

This application is a Continuation-In-Part of application Ser. No. 08/721,368, filed on Sep. 26, 1996.

BACKGROUND OF THE INVENTION

1. Field of the Invention

The subject invention relates to a 0.197" (5 mm) needle for making injections into the subcutaneous layer in the tissue "strata" of a patient and, more particularly, a 5 mm needle having a 31 gauge cannula for use on a medication delivery pen or hypodermic syringe.

2. Background Description

Medication delivery pens are hypodermic syringes used for self-injection of precisely measured doses of medication. Pens are widely used, for example, by diabetics to dispense insulin.

A typical prior art medication delivery pen includes a cartridge which contains a volume of liquid medication sufficient for several doses. The cartridge includes an elongated generally tubular glass cartridge having a pierceable rubber septum which extends across the open distal end of the cartridge and is securely held in position by a metallic sleeve that is crimped to the distal end of the cartridge. The cartridge also includes a rubber stopper in sliding fluid-tight engagement with interior walls of the cartridge.

Such a medication delivery pen also includes a unitarily molded cartridge retainer having a small diameter tubular neck dimensioned for tightly engaging the neck of the cartridge and the metallic sleeve crimped thereon so as to support and position the entire cartridge. Exterior regions at the extreme distal end of the tubular neck are formed with an array of threads for threadedly receiving the mounting cap of a needle assembly. The medication delivery pen further includes a dosing apparatus that is engaged with the proximal end of the cartridge retainer having a plunger for engaging the rubber stopper of the cartridge. The dosing apparatus includes a dose setting structure used to select the longitudinal distance through which the plunger will move, and dispensing means for driving the plunger the selected distance.

The needle assembly for the medication delivery pen includes an elongate needle cannula having opposed proximal and distal points and a lumen extending therethrough. A plastic cork is adhered to an intermediate position along the needle cannula and in turn is rigidly connected to an end wall of a cylindrical cap. The cylindrical wall of the cap surrounds the proximal point on the needle cannula and includes an array of internal threads for engaging the external threads on the neck of the cartridge retainer.

The medication delivery pen may be used by urging the cap of the needle assembly over the neck of the cartridge retainer sufficiently for the proximal point of the needle cannula to pierce the rubber septum of the cartridge. The cap is then rotated to threadedly engage the neck of the cartridge retainer. The user then manipulates the dosing apparatus to select an appropriate dose. A protective shield over the distal end of the needle cannula is then removed, and the distal point of the needle cannula is injected. The user then actuates the dispensing means of the prior art dosing apparatus to urge the stopper of the cartridge distally and to deliver medication through the lumen of the needle cannula. The needle is then withdrawn, and the needle assembly is separated from the cartridge retainer and safely discarded. The rubber septum of the cartridge reseals itself, and may be pierced again for a subsequent administration of medication. This process may be carried out repeatedly until all of the medication in the cartridge has been used.

A problem with currently available needle assemblies for use on medication delivery pens is the size of the cannula. Prior to the present invention, 27, 28, 29 and 30 gauge needle cannulas have been commonly used on medication delivery pens, with 30 gauge being the smallest diameter possible. Even though smaller gauges, i.e., 29 and 30 gauge, have helped to reduce pain to patients during injection, there is still a need to provide needle assemblies for medication delivery pens with smaller cannula diameters since small diameter needles are perceived by patients to cause less pain during the injection. However, no one skilled in the art has suggested and no one has provided patients with needle assemblies having a diameter less than 30 gauge.

Another problem with currently available needle assemblies for use on medication delivery pens or with hypodermic syringes is the need for the user or patient to "pinch up" at the injection site to ensure that the injection of the medication is into subcutaneous tissue. It has been found that injections of medication into the muscle layer can be painful. Therefore, it is desirable to have a new needle assembly for use on medication delivery pens and hypodermic syringes that eliminates the need for "pinch up" and deliver a dose of medication to a proper location in the tissue "strata".

SUMMARY OF THE INVENTION

The present invention overcomes the 30 gauge limit that has existed for pen needle assemblies by providing a 31 gauge needle assembly for use on medication delivery pens. The 31 gauge needle provides a patient with a needle assembly having a smaller cannula size without loss in performance or structural integrity. The 31 gauge needle assembly mounts on a needle mounting tip of a cartridge retainer assembly on a medication delivery pen and is used like prior art needle assemblies to pierce a patient's arm during an injection process.

However, since the 31 gauge needle cannula is smaller than prior art needle cannulas the penetration force is decreased which reduces the pain caused during an injection procedure. In addition, the smaller cannula size will be seen by the patient prior to the injection so that perceived pain or anticipated pain is also reduced. The reduction in actual and perceived/anticipated pain provided by using the 31 gauge needle on the medication delivery pen is a major benefit to patients that need numerous injections each day, i.e., diabetics requiring insulin injections.

Another aspect of the present invention is providing a needle having a minimal usable length that can deliver a dose of medication to a proper location in the tissue "strata" or subcontinuous layer. The present invention provides a needle with a usable length of 5 mm for making such an injection and medication delivery, wherein the need for the user or patient to "pinch-up" the skin layer during the injection is eliminated.

These and other aspects, features and advantages of the present invention will become apparent from the following detailed description taken in conjunction with the accompanying drawings.

BRIEF DESCRIPTION OF THE DRAWINGS

FIG. 3 is a perspective view of a hypodermic syringe having a permanently mounted needle assembly according to the present invention; and FIG. 4 is an exploded perspective view of a hypodermic syringe having a removably mounted needle assembly according to the present invention.

DETAILED DESCRIPTION OF THE PREFERRED EMBODIMENT

Figure 1:
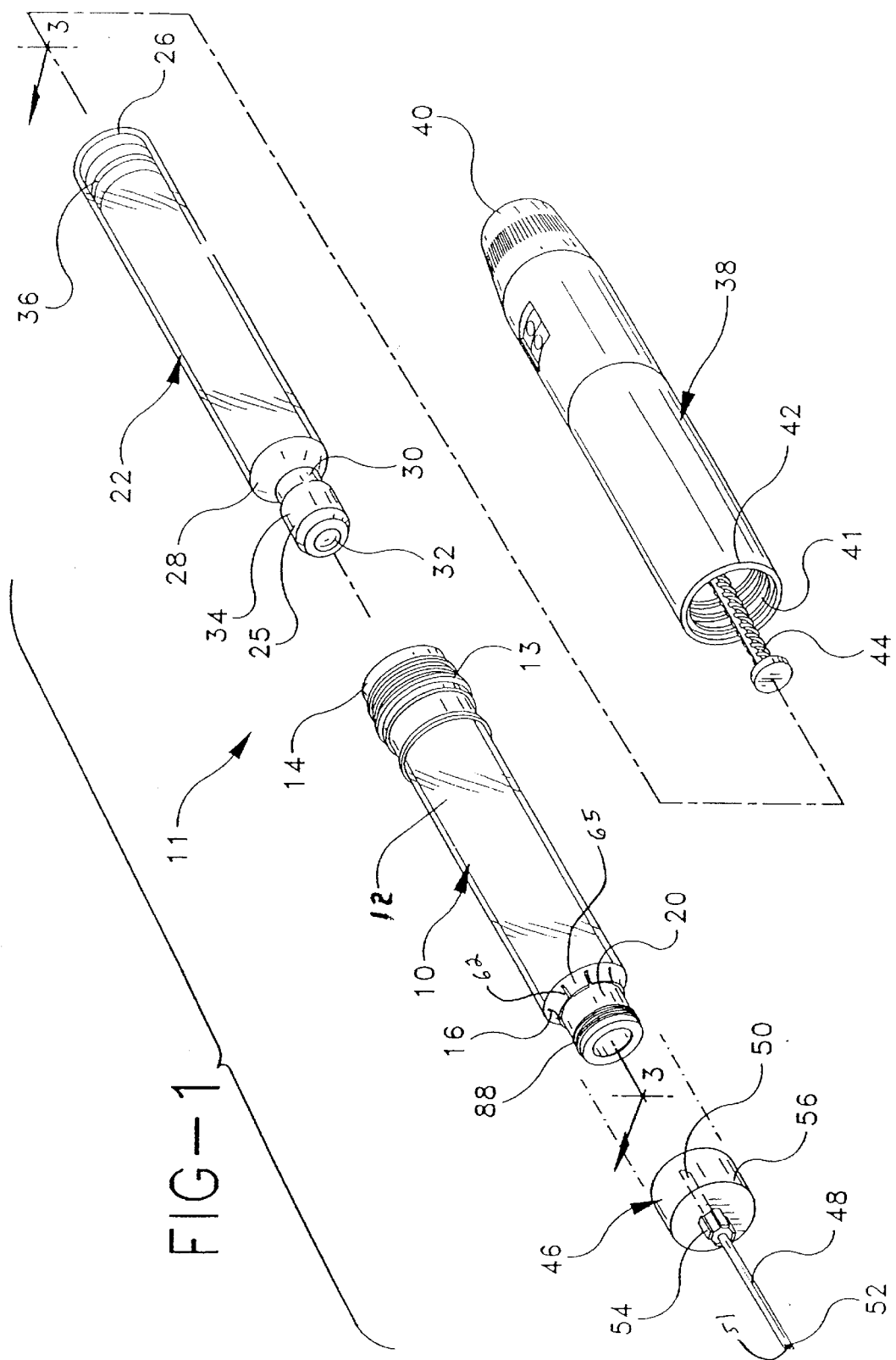
FIG. 1 is an exploded perspective view of a medication delivery pen having a needle assembly in accordance with the subject invention.

A needle assembly for use on a medication delivery pen 11, in accordance with the subject invention, is identified generally by the numeral 46 in FIG. 1. As shown in FIG. 1 medication delivery pen 11 includes a cartridge retainer assembly 10, a dosing apparatus 38 and a cartridge assembly 22. Needle assembly 46, as described in more detail below, is designed to be attached to a needle mounting insert tip 20 on cartridge retainer assembly 10.

Figure 2:
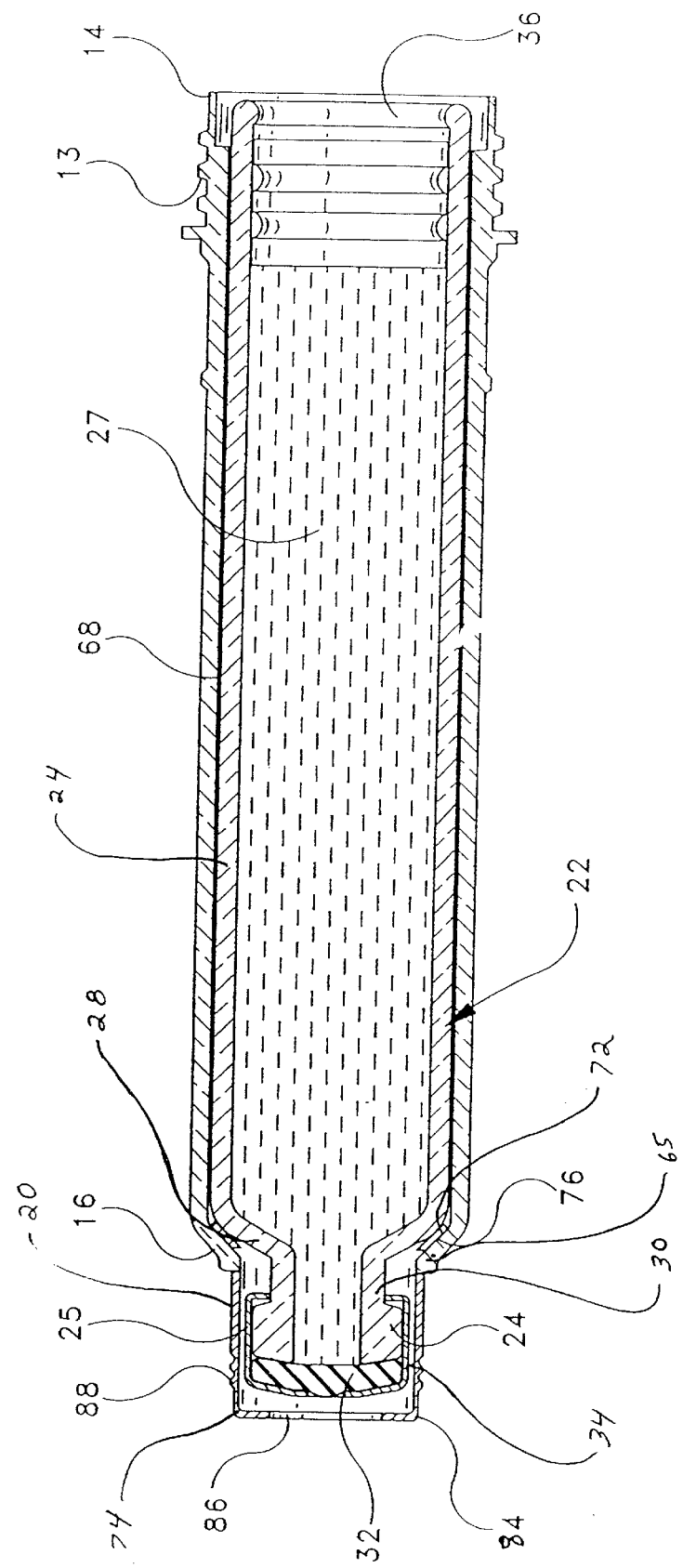
FIG. 2 is a cross-sectional view of a cartridge retainer assembly of the medication delivery pen.

Cartridge retainer assembly 10, as shown in FIGS. 1 and 2, includes an elongate generally tubular body 12 with opposed proximal and distal ends 14 and 16, respectively. A generally tubular needle mounting insert tip 20 is snap-fit mounted in distal end 16 of body 12 and cartridge retainer assembly 10 is dimensioned and configured to receive a cartridge assembly 22 therein.

Cartridge assembly 22 includes an open proximal end 26 and a distal end 25 defined by an inwardly converging shoulder 28. A small diameter neck 30 projects distally from shoulder 28 on cartridge assembly 22, and is provided with a large diameter annular bead 24, shown in FIG. 2, extending circumferentially thereabout at the extreme distal end of neck 30. A pierceable and resealable rubber septum 32 extends completely across the open distal end defined by neck 30. Rubber septum 32 is held in place by a metallic sleeve 34 which is crimped around bead 24 at the distal end of neck 30. Medication 27 such as insulin or heparin is pre-filled into cartridge assembly 22 and is retained therein by a rubber stopper 36. Stopper 36 is in sliding fluid-tight engagement with the tubular wall of cartridge assembly 22. Distally directed forces on stopper 36 urge the medication 27 from pen 11 as explained further below.

Dosing apparatus 38 in medication delivery pen 11 is generally cylindrical and includes opposed proximal and distal ends 40 and 42, respectively. Threads 41 are disposed at distal end 42 of dosing apparatus 38 for releasable threaded engagement with proximal end 14 of body 12 of cartridge retainer assembly 10. A plunger rod 44 projects distally from dosing apparatus 38 and is dimensioned to engage stopper 36 of cartridge assembly 22. Dosing apparatus 38 also includes known mechanisms for setting a selected dose of medication to be delivered by pen 11. A dispensing mechanism (not shown) is operative to drive plunger rod 44 a selected distance in a distal direction for moving stopper 36 a distance that will inject the selected dose of medication from cartridge assembly 22. Although a particular prior art dosing apparatus 38 is depicted in FIG. 1, it is to be understood that other dosing apparatus can be used with the needle assembly of the subject invention.

Needle assembly 46, according to the present invention, includes a 31 gauge needle cannula 48 with opposed proximal and distal tips 50 and 52, respectively, and a lumen 51 extending entirely therethrough. The dimensions of 31 gauge needle cannula 48 are set forth below:

| Parameter | Value |
| --- | --- |
| Outer Diameter | 0.010"–0.0105" |
| Inner Diameter | 0.0045"–0.006" |
| Wall Thickness | 0.00225"–0.00275" |
| Usable length | 0.315" (8 mm) |
| Cannula Material | Stainless Steel |

Of course, 31 gauge needle cannulas of other usable lengths can also be used, i.e., 0.236" (6 mm) or 0.394" (10 mm), and still remain within the scope of the present invention. A cork 54 is securely affixed at an intermediate position along needle cannula 48, and a cap 56 is securely affixed to cork 54. Cap 56 of needle assembly 46 includes an array of internal threads (not shown) for removable mounting needle assembly 46 to needle mounting insert tip 20 on cartridge retainer assembly 10. It is to be understood, however, that other releasable engagement means between needle assembly 46 and cartridge retainer assembly 10 can be provided. For example, external threads can be formed on needle assembly 46 and corresponding internal threads can be defined on cartridge retainer assembly 10 or a bayonet style mount using lugs and slots can be used. In addition, needle assembly 46 could be "snap fit" on to cartridge retainer assembly 10.

As shown in FIG. 1, body 12 of cartridge retainer assembly 10 includes a plurality of inwardly projecting supports 65 separated from one another by notches 62, wherein supports 65 are used to hold insert tip 20 in distal end 16 of cartridge retainer assembly 10. FIG. 2 is a cross-sectional view of cartridge retainer assembly 10 that shows cartridge assembly 22 within a cartridge receiving chamber 68. FIGS. 1 and 2 also show an array of threads 13 on proximal end 14 of body 12 used to engage threads 41 on distal end 42 of dosing apparatus 38.

Needle mounting insert tip 20 of cartridge retainer assembly 10 includes opposed proximal and distal ends 72 and 74, respectively. As shown in FIG. 2, proximal end 72 of needle mounting insert tip 20 includes a rim 76 extending therefrom that is diametrically dimensioned to closely engage metallic sleeve 34 crimped to cartridge assembly 22 for holding rubber septum 32 in place. Distal end 74 of needle mounting insert tip 20 includes a generally annular end wall 84 having an aperture 86 extending therethrough for access by proximal point 50 of needle cannula 48. An array of outwardly disposed threads 88 is defined intermediate proximal and distal ends 72 and 74, respectively. Threads 88 are disposed and dimensioned for engaging threads on needle assembly 46.

Assembly of medication delivery pen 11 is performed by inserting cartridge assembly 22 into cartridge retainer assembly 10. More particularly, neck 30 and crimped metallic sleeve 34 of cartridge assembly 22 are inserted in a proximal to distal direction into open proximal end 14 of body 12 of cartridge retainer assembly 10. Crimped metallic sleeve 34 eventually will pass entirely through body 12, and further advancement of cartridge assembly 22 into cartridge retainer assembly 10 will require entry of crimped metallic sleeve 34 into rim 76 extending from proximal end 72 of needle mounting insert tip 20. Considerable dimensional variation and eccentricities between the neck and body of prior art cartridges are known to exist. If such eccentricities do exist, crimped metallic sleeve 34 will rest on rim 76 of insert tip 20 to center sleeve 34 relative to body 12 into a position that conforms with any dimensional inconsistencies or eccentricities in cartridge assembly 22.

Further distally directed movement of cartridge assembly 22 into cartridge retainer assembly 10 will cause shoulder 28 of cartridge assembly 22 to seat against rim 76 of insert tip 20. Rim 76 therefore defines the fully seated position of cartridge assembly 22 in cartridge retainer assembly 10 and functions to securely engage cartridge assembly 22. In this fully seated position, as shown most clearly in FIG. 2, septum 32 of cartridge assembly 22 is spaced proximally from distal wall 84 of needle mounting insert tip 20. Dosing apparatus 38 is then assembled to proximal end 14 of the body of cartridge retainer assembly 10 such that plunger rod 44 of dosing apparatus 38 engages stopper 36 of cartridge assembly 22.

Medication delivery pen 11 is used by mounting needle assembly 46 to needle mounting insert tip 20 of cartridge retainer assembly 10. This mounting is achieved by moving needle assembly 46 in a proximal direction over needle mounting insert tip 20 until the threads (not shown) of cap 56 engage external threads 88 on needle mounting insert tip 20. Threads 88 of needle mounting insert tip 20 are spaced from the extreme distal end of needle mounting insert tip 20, therefore, the initial axial advancement of cap 56 over needle mounting insert tip 20 will cause proximal point 50 of needle cannula 48 to pierce rubber septum 32 of cartridge assembly 22 prior to rotational threaded engagement of needle assembly 46 with needle mounting insert tip 20. Thus, the bevel which defines proximal point 50 will advance axially through septum 32 without a rotation that could tear rubber septum 32.

After threads of cap 56 engage threads 88 of needle mounting insert tip 20, further advancement of needle assembly 46 requires relative rotation between cap 56 and needle mounting insert tip 20. It will be appreciated that needle mounting insert tip 20 is too small to be readily griped by the user of medication delivery pen 11, and is partly covered by cap 56. However, the relative rotation can be achieved by rotating body 12 of cartridge retainer assembly 10. Since needle mounting insert tip 20 is locked to distal end 16 on body 12 of cartridge retainer assembly 10, rotation of body 12 is transmitted to needle mounting insert tip 20 and enables complete rotational engagement of needle assembly 46.

Use of medication delivery pen 11 proceeds in a conventional manner with dosing apparatus 38. Actuation of dosing apparatus 38 causes liquid medication in cartridge assembly 22 to be urged in a distal direction through lumen 51 of needle cannula 48. This distally directed liquid pressure also will cause septum 32 to distend in a distal direction. However, as noted above and as shown in FIG. 2, septum 32 is spaced proximally from cork 54 of needle assembly 46, and will not be urged into contact with cork 54. Thus, drooling or weeping of liquid medication can be substantially prevented. This is enabled because cartridge assembly 22 is supported and accurately positioned by engagement of cartridge shoulder 28 with rim 76 on insert tip 20. Hence neck 30 and crimped metallic sleeve 34 need not be closely engaged by needle mounting insert tip 20. After medication delivery pen 11 has been used, needle assembly 46 is separated from needle mounting insert tip 20 and discarded.

More recently, a new design for a needle assembly 46, shown in FIG. 1, has been developed that includes a needle cannula 48 with opposed proximal and distal tips 50 and 52, respectively, and a lumen 51 extending entirely therethrough, wherein needle cannula 48 has a usable length of 0.197" (5 mm) that provides a number of substantial benefits. The new design is also usable with standard hypodermic syringes, like those shown in FIGS. 3 and 4, that provide similar benefits. One of the most substantial benefits provided by the new design is its capability of delivering a dose of medication to a proper location in the tissue "strata" or subcontinuous layer without the need for the user or patient to "pinch-up" the skin layer during the injection. It has been found that a 5 mm needle provides this function.

An example of the newly designed needle assembly 46, according to the present invention for use as a medication delivery pen, includes the following dimensions:

| Parameter | Value |
| --- | --- |
| Outer Diameter | 0.010"–0.0105" |
| Inner Diameter | 0.0045"–0.006" |
| Wall Thickness | 0.00225"–0.00275" |
| Usable length | 0.197" (5 mm) |
| Cannula Material | Stainless Steel |

FIG. 3 is a perspective view of a hypodermic syringe 100 including a barrel 110, a plunger 120 slidably mounted therein, and a needle assembly 125 permanently mounted to distal end 111 of housing 110. As shown, needle assembly 125 includes a hub 130 with a needle cannula 131 mounted therein having a usable length of cannula 131 extending from hub 130 is a distal direction. As discussed above, needle cannula 131 can be of any gauge and more importantly has a usable length of 0.197" (5 mm) to provide the benefits of delivering a dose of medication to a proper location in the tissue "strata" or subcutaneous layer without the need for the user or patient to "pinch-up" the skin layer during the injection. Needle cannula 131 is preferably 31 gauge to minimize any pain during the injection process, however, larger gauges could also be used and still fall within the scope of the present invention.

FIG. 4 shows an alternative hypodermic syringe 200, wherein needle assembly 210 is removably mounted to a distal end 221 of a housing 220. Needle assembly 210 includes a hub 213 having a needle cannula 211 having a usable length of 0.197" (5 mm) extending in the distal direction and a pair of tabs 212 extending from a proximal end of hub 213. Tabs 212 are made to engage with threads 222 at distal end 221 of housing 220 and hold needle assembly 210 on housing 220. Since 5 mm needle assembly 210, according to the present invention, is removably attached to hypodermic syringe housing 220 multiple injections using housing 220 can be performed using a new 5 mm needle assembly 210 for each injection.

In the foregoing discussion, it is to be understood that the above-described embodiments of the present invention are simply illustrative of various features of a cartridge retainer assembly for a medication delivery pen. Other suitable variations, modifications and combinations of these features could be made to or used in these embodiments and still remain within the scope of the present invention.

What is claimed is:

1. A needle assembly comprising:
   a needle hub; and
   a 31 gauge needle cannula mounted in said needle hub, said cannula having a distal tip and a usable length between said needle hub and said distal tip of 0.197 inches so to deliver a dose of medication to a proper location in a tissue without the need for a user to pinch-up a skin layer during the injection.

2. A needle assembly according to claim 1, wherein said cannula has an outer diameter less than 0.0105 inches.

3. A needle assembly according to claim 1, wherein said cannula has an outer diameter no smaller than 0.010 inches and no larger than 0.0105 inches.

4. A needle assembly according to claim 1, wherein said cannula has an inner diameter no smaller than 0.0045 inches and no larger than 0.006 inches.

5. A needle assembly according to claim 1, wherein said cannula is made of stainless steel.

6. A needle assembly according to claim 1, wherein said cannula has a wall thickness no smaller than 0.00225 inches and no larger than 0.00275 inches.

7. A hypodermic syringe comprising:

a housing having a distal end;

a plunger slidably mounted within said housing; and a needle assembly mounted on said distal end of said housing, said needle assembly comprising:
  a needle hub; and
    a 31 gauge needle cannula mounted in said needle hub, said cannula having a distal tip and a usable length between said needle hub and said distal tip of 0.197 inches so to deliver a dose of medication to a proper location in a tissue without the need for a user to pinch-up a skin layer during the injection.

8. A needle assembly according to claim 7, wherein said needle assembly is permanently mounted on said housing.

9. A needle assembly according to claim 7, wherein said needle assembly is removably mounted to said housing.

10. A pen needle assembly for use with a medication delivery pen, said pen needle assembly comprising:

a needle hub for mounting said pen needle on a medication delivery pen; and a 31 gauge needle cannula mounted in said needle hub and having a proximal tip, a distal tip, and a usable length between said needle hub and said distal tip of 0.197 inches so to deliver a dose of medication to a proper location in a tissue without the need for a user to pinch-up a skin layer during the injection.

* * * * *